(12) United States Patent
Wang

(10) Patent No.: US 10,595,800 B2
(45) Date of Patent: Mar. 24, 2020

(54) SUPPORT APPARATUS FOR XRAY DETECTOR AND XRAY DETECTING APPARATUS

(71) Applicant: GENERAL ELECTRIC COMPANY, Schenectady, NY (US)

(72) Inventor: Xiaojie Wang, Beijing (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 410 days.

(21) Appl. No.: 15/296,877

(22) Filed: Oct. 18, 2016

(65) Prior Publication Data

US 2017/0119328 A1    May 4, 2017

(30) Foreign Application Priority Data

Oct. 30, 2015 (CN) .......................... 2015 1 0727268

(51) Int. Cl.
*A61B 6/00* (2006.01)
(52) U.S. Cl.
CPC .............. *A61B 6/4429* (2013.01); *A61B 6/42* (2013.01)
(58) Field of Classification Search
None
See application file for complete search history.

(56) References Cited

U.S. PATENT DOCUMENTS

| | | | | |
|---|---|---|---|---|
| 4,538,293 A | * | 8/1985 | Cutter ................. | G03B 42/025 378/181 |
| 4,589,124 A | * | 5/1986 | Ruiz .................... | G03B 42/025 280/304.1 |
| 5,224,148 A | * | 6/1993 | Baker, Jr. ............. | G03B 42/025 378/167 |
| 5,255,304 A | * | 10/1993 | Uffinger ............... | G03B 42/045 378/170 |

\* cited by examiner

*Primary Examiner* — Hoon K Song
(74) *Attorney, Agent, or Firm* — Fletcher Yoder, P.C.

(57) ABSTRACT

The present invention provides a support device for an X-ray detector and an X-ray detection device, the support device comprising a bottom plate and a limiting device mounted on the bottom plate, the limiting device comprising a limiting frame, two mounting members connected to the limiting frame, and two stoppers respectively arranged on the two mounting members. At least one of the two mounting members is configured to be able to move in a particular direction and to be limited at one of a plurality of fixed positions on the limiting frame, and the two stoppers are used for limiting the movement of the X-ray detector in the particular direction.

16 Claims, 3 Drawing Sheets

SUPPORT APPARATUS FOR XRAY DETECTOR AND XRAY DETECTING APPARATUS

CROSS-REFERENCE TO RELATED APPLICATIONS

This application claims foreign priority benefits under 35 U.S.C. 119(a) to Chinese Application No. 201510727268.X, filed on Oct. 30, 2015, which is incorporated herein by reference in its entirety.

TECHNICAL FIELD

The present invention relates to the field of medical imaging, in particular to a support device for an X-ray detector and to an X-ray detection device.

BACKGROUND

During X-ray medical diagnosis, an X-ray detector is generally installed in X-ray detection equipment by means of a support device, so as to receive the X-rays passing through the object to be detected and output electrical signals for image reconstruction.

The support device for an X-ray detector is generally a tray similar to a drawer. The tray is provided with opposite baffles, with a distance between the opposite baffles being constant and adapted to the size of the X-ray detector. Before the X-ray detection equipment starts to work, the tray can be pulled to the outside so that the X-ray detector can be installed in the tray and the signal interface of the X-ray detector is mated with the signal interface on the tray, and then the tray is pushed into the X-ray detection equipment, so as to be ready for X-ray detection.

In order to meet the needs of different applications and for easy operations, there is a need to design a support device, which facilitates the replacement with X-ray detectors having different sizes on the support device, so that X-ray detectors having different sizes can be applied to the same X-ray detection equipment for X-ray detection, without needing to equip a corresponding support device for each model of X-ray detector.

SUMMARY

One object of the present invention is to provide a support device for an X-ray detector and an X-ray detection device, which can facilitate the replacement with X-ray detectors having different sizes.

An exemplary embodiment of the present invention provides a support device for an X-ray detector, comprising a bottom plate and a limiting device mounted on the bottom plate, the limiting device comprising a limiting frame, two mounting members connected to the limiting frame, and two stoppers respectively arranged on the two mounting members. At least one of the two mounting members can move in a particular direction and can be limited at one of a plurality of fixed positions on the limiting frame, and the two stoppers are used for limiting the movement of the X-ray detector in the particular direction.

The exemplary embodiment of the present invention further provides an X-ray detection device, comprising an X-ray detector and the above-mentioned support device for an X-ray detector.

Other features and aspects will become apparent from the following detailed description, the drawings, and the claims.

BRIEF DESCRIPTION OF THE DRAWINGS

The present invention will be better understood by the description for the exemplary embodiments of the present invention in conjunction with the accompanying drawings. In the drawings.

DETAILED DESCRIPTION

The specific embodiments of the present invention will be described below; it should be noted that, in the specific description of these embodiments, for brief descriptions, the specification could not describe all the features of the actual implementations in an exhaustive way. It should be understood that, in the actual implementation of any embodiment, just as in the course of any engineering project or design project, in order to achieve the developers' specific goals and in order to meet system-related or business-related restrictions, a variety of concrete decisions will be made accordingly, which will change from one embodiment to another embodiment. Furthermore, it should be understood that, although the efforts made in this development process may be complicated and lengthy, but for those skilled in the art related to the content disclosed in the present invention, on the basis of the technical content disclosed in this disclosure, some changes in the design, manufacture or production are merely conventional technical means, and it should not be construed as the content of the present disclosure being insufficient.

Unless otherwise defined, technical or scientific terms used in the claims and specification should have the general meaning understood by those skilled in the art related to the present invention. The terms "first", "second" and the like used in the specification and the claims in the present invention are merely used to distinguish different components, rather than denoting any order, quantity, or importance. The term "one" or "a" or the like denotes the presence of at least one, rather than representing a quantitative restriction. The term "comprising" or "including" or the like means that the element or object before the term "comprising" or "including" encompasses the element or object or equivalent element listed after the term "comprising" or "including" while not excluding other elements or objects. The term "connected" or "connected to each other" or the like is neither limited to physical or mechanical connections, nor to direct or indirect connections.

Figure 1:
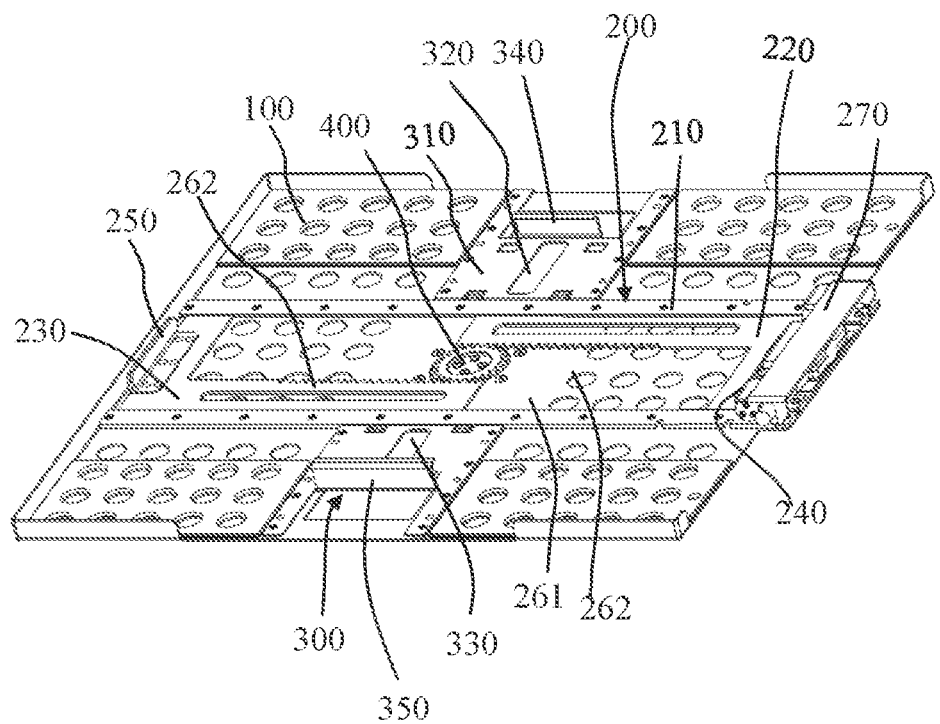
FIG. 1 is a structural schematic view of a support device for an X-ray detector provided by an embodiment of the present invention.

FIG. 1 is a structural schematic view of a support device for an X-ray detector provided by an embodiment of the present invention. As shown in FIG. 1, the present invention provides a support device for an X-ray detector, comprising a bottom plate 100 and a limiting device mounted on the bottom plate 100, and the limiting device may comprise, for example, a first limiting device 200 and/or a second limiting device 300 in FIG. 1, and the number of the limiting device may be one or more. In the embodiment of the present invention, the limiting device may be pivotally connected to the bottom plate 100, and when the support device for an X-ray detector comprises a plurality of limiting devices, the plurality of limiting devices are stacked in sequence and pivotally connected to the bottom plate 100 by means of a common pivot shaft. For example, in the support device for an X-ray detector as shown in FIG. 1, the first limiting device 200 is stacked on the second limiting device 300, and the first and second limiting devices are pivotally connected to the bottom plate 100 by means of a common pivot shaft 400; therefore, the first limiting device 200 and the second limiting device 300 may respectively rotate around the pivot shaft 400 relative to the bottom plate 100, so as to facilitate replacing the detector.

The above-mentioned limiting device comprises a limiting frame, two mounting members connected to the limiting frame, and two stoppers respectively arranged on the above-mentioned two mounting members. At least one of the above-mentioned two mounting members can move in a particular direction, and can be limited at one of the plurality of fixed positions on the limiting frame. The above-mentioned two stoppers are used for limiting the movement of the X-ray detector in the particular direction. In the first limiting device 200, the above-mentioned particular direction may comprise a first direction, for example, the horizontal direction in FIG. 1; and in the second limiting device 300, the above-mentioned particular direction may comprise a second direction, for example, the vertical direction in FIG. 1.

Figure 2:
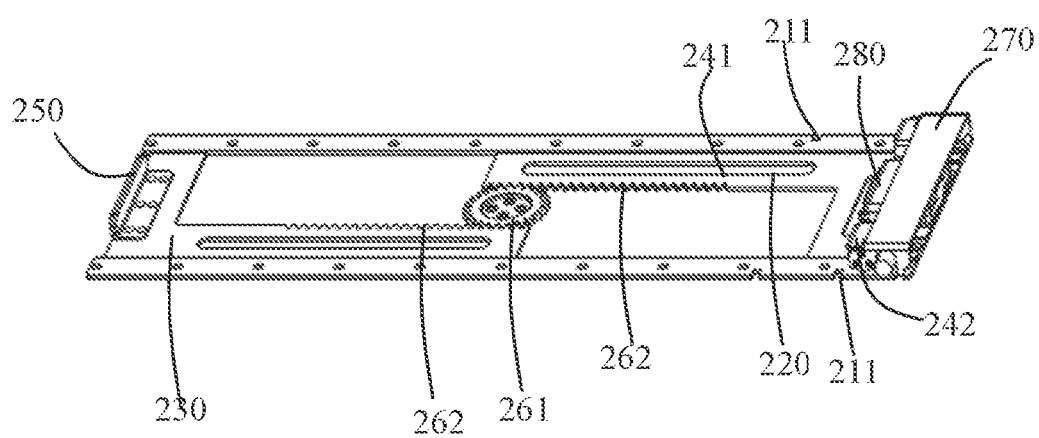
FIG. 2 is a structural schematic view of a first limiting device in FIG. 1.

FIG. 2 is a structural schematic view of a first limiting device in FIG. 1. As shown in FIGS. 1 and 2, the above-mentioned first limiting device 200 may comprise a limiting frame 210, two mounting members 220 and 230, and two stoppers 240 and 250. The mounting members 220 and 230 may be connected to the limiting frame 210, so that the mounting members 220 and 230 can move in the first direction and can be limited at one of the plurality of fixed positions on the limiting frame 210. In this way, the positions of the stopper 240 on the mounting member 220 and the stopper 250 on the mounting member 230 may be adjusted by driving the movement of the mounting members 220 and 230, and the mounting members 220 and 230 may be limited when moving to a fixed position, so that the distance between the stoppers 240 and 250 may be adjusted and adapted to the size of one or more X-ray detectors.

Further, the mounting members 220 and 230 can synchronously move towards each other or away from each other in the first direction. Allowing the mounting members 220, 230 to move towards each other or away from each other not only achieves the decrease or increase in distance between the stoppers 240, 250, but also avoids the offset of the center of the space between the stoppers 240, 250 and thus avoids the offset of the center of the X-ray detector after the replacement with an X-ray detector of a different size, by the synchronous movement of the mounting members 220, 230.

In an embodiment, the first limiting device 200 may further comprise a gear 261, and the gear 261 may be mounted on the bottom plate 100. In the first limiting device 200, each of the two mounting members 220, 230 is provided with a spur gear 262, and the spur gears 262 on the mounting members 220, 230 are parallel to each other and are engaged with the gear 261. When one of the mounting members 220, 230 moves in the first direction, the spur gear 262 on the mounting member cooperates with the gear 261, so that the other mounting member 230 moves along with the mounting member towards or away from the mounting member. In another embodiment, the mounting members 220 and 230 may synchronously move towards each other or away from each other in other ways, for example, by driving electronically.

In the embodiment of the present invention, the first limiting device 200 may be pivotally connected to the bottom plate 100 by the gear 261, for example, the gear 261 is pivotally connected to the bottom plate 100 by means of a pivot shaft 400, so that the first limiting device 200 can rotate around the pivot shaft 400 relative to the bottom plate 100.

As shown in FIG. 2, specifically, in the first limiting device 200, the limiting frame 210 may comprise two parallel guide bars arranged in the first direction. Each of the mounting members 220 and 230 comprises a sliding piece and a mounting piece, the sliding piece and the mounting piece of each of the mounting members being connected to each other to form an L-shaped structure. The sliding pieces of the mounting members 220 and 230 are parallel to each other, and are configured to be respectively mounted on two guide bars of the limiting frame 210 and to be able to slide under the guidance of the corresponding guide bars. For example, when the mounting member 220 is driven, the above-mentioned gear and spur gear structure actuates the mounting member 230 to also move towards or away from the mounting member 220 in the first direction.

Optionally, the first limiting device 200 further comprises a limiting handle 270, and the limiting handle 270 is arranged on at least one of the mounting members 220 and 230.

Figure 3:
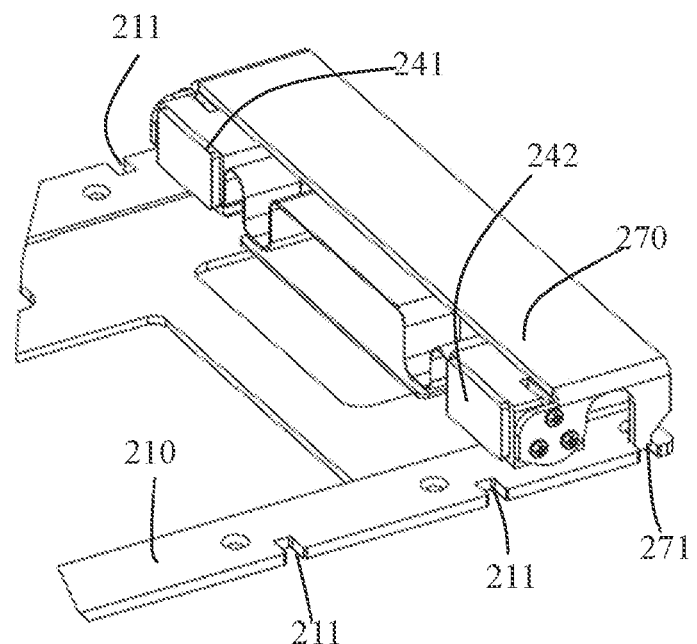
FIG. 3 is a structural schematic view of a limiting handle in FIG. 1.
Figure 4:
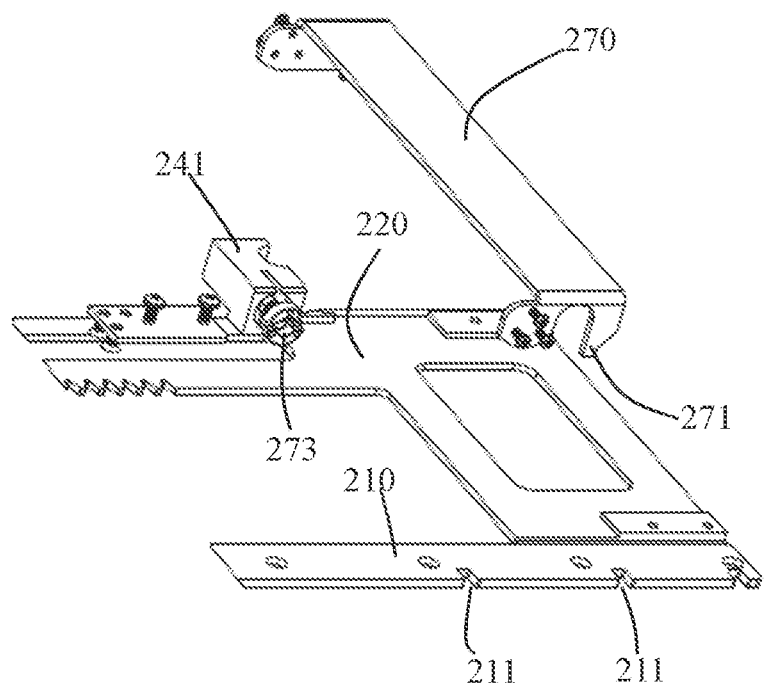
FIG. 4 is an exploded view of the limiting handle in FIG. 3.

FIG. 3 is a structural schematic view of the limiting handle in FIG. 1, and FIG. 4 is an exploded view of the limiting handle in FIG. 3. As shown in FIGS. 3 and 4, the limiting handle 270 is provided with a first limiting protrusion 271, and first limiting slots 211 are arranged at a plurality of fixed positions on the limiting frame 210 of the first limiting device 200. The limiting handle 270 can move along with the corresponding mounting member 220 or 230 when the limiting handle is at a first position (release position), and fit with a first limiting slot 211 when the limiting handle is at a second position (locked position). For example, when the limiting handle 270 is at the first position, the first limiting protrusion 271 is located outside all of the first limiting slots 211, and then the corresponding mounting member 220 or 230 and its stopper 240 or 250 may be driven by, for example, pushing or pulling the limiting handle 270, so as to move in the first direction; and when the limiting handle 270 is at the second position, the first limiting protrusion 271 may be received in a first limiting slot 211, so that the first limiting slot 211 and the first limiting protrusion 271 abut against each other to stop the movement of the corresponding mounting member 220 or 230 in the first direction.

Optionally, the limiting handle 270 is hinged with the stopper 240 or 250 on the corresponding mounting member 220 or 230, and the limiting handle 270 may rotate relative to the corresponding stopper 240 or 250 to the above-mentioned first or second position. For example, as shown in FIG. 1, the limiting handle 270 may comprise a top plate and a side wall extending downwards from the top plate, and the side wall of the limiting handle 270 extends downwards to form the above-mentioned first limiting protrusion 271. The side wall of the limiting handle 270 is hinged with the two ends of the stopper 240, so that the limiting handle 270 can rotate. When it is needed to drive the mounting member 220, the top plate of the limiting handle 270 can be operated to rotate the limiting handle 270 so as to turn the top plate upwards, so that the limiting handle 270 is at the first position, and then the top plate can be operated to move the mounting member 220 in the first direction; when the mounting member has moved to any of the above-mentioned fixed positions on the limiting frame 210, the limiting handle 270 can be released so as to rotate to the second position, so that the first limiting protrusion 271 fits with the first limiting slot 211 at the fixed position.

Specifically, the above-mentioned limiting handle 270 may be hinged with the corresponding stopper 240 or 250 by a spring hinge 273, so that by means of the spring hinge 273, the limiting handle 270 may automatically return from the first position to the second position when released, facilitating easy operation.

Specifically, the above-mentioned stopper 240 may comprise two stop blocks 241 and 243 arranged opposite to each other on the mounting member 220, and the stopper 250 may be particularly a stop piece or a stop hook. Two ends (for example, two side walls) of the limiting handle 270 may be respectively hinged with the stop blocks 241 and 243 or respectively hinged with two ends of the stopper 250, so as to improve the mechanical stability.

Figure 5:
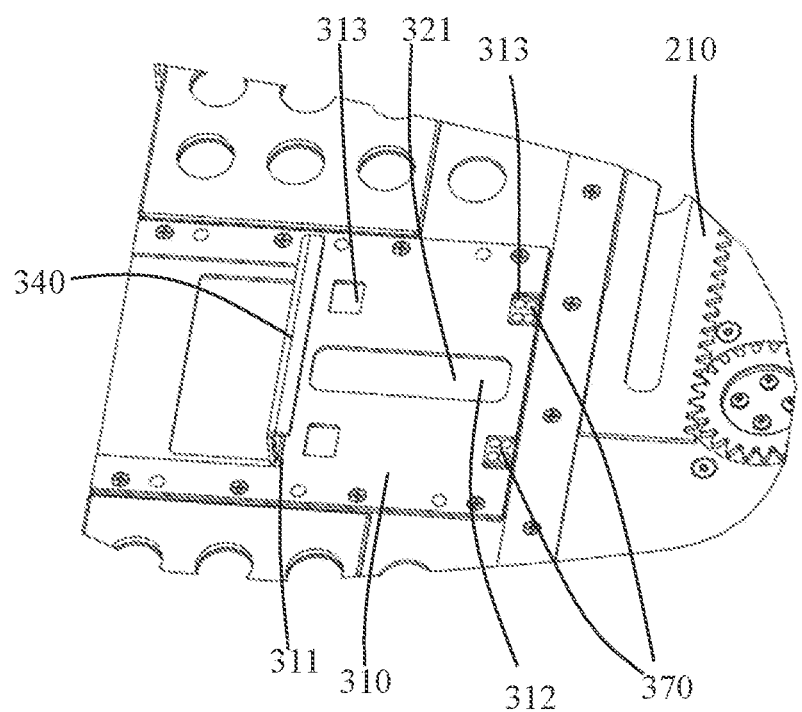
FIG. 5 is a structural schematic view of a second limiting device in FIG. 1.

FIG. 5 is a structural schematic view of the second limiting device in FIG. 1. As shown in FIGS. 1 and 5, the second limiting device 300 may comprise a limiting frame 310, two mounting members 320 and 330, and two stoppers 340 and 350. The limiting frame 310 may be mounted on the bottom plate 100. The mounting members 320 and 330 may be connected to the limiting frame 310, and the mounting members 320 and 330 can move in a second direction and can be limited at one of the plurality of fixed positions on the limiting frame 310. In this way, the positions of the stopper 340 on the mounting member 320 and of the stopper 350 on the mounting member 330 may be adjusted by driving the movement of the mounting members 320 and 330, and the mounting members 320 and 330 may be limited when having moved to a fixed position, so that the distance between the stoppers 340 and 350 may be adjusted and adapted to the size of one or more X-ray detectors.

Specifically, at least one of the two mounting members 320 and 330 of the second limiting device 300 may comprise an elastic piece, the limiting frame 310 may be provided with a sliding guide slot, and the above-mentioned elastic piece, in a first state, may be slide in the second direction under the guidance of the sliding guide slot.

For example, the mounting member 320 may comprise an elastic piece 321, and the limiting frame 310 may be provided with a sliding guide slot 311. The mounting member 320 may be provided with a groove 312 in communication with the sliding guide slot 311, and when the elastic piece 321 is pressed in the groove 312, the elastic piece 321 is in the first state, and then the stopper 340 on the mounting member 320 may be operated to drive the elastic piece 321 to move in the sliding guide slot 311.

Optionally, the above-mentioned elastic piece 321 may be provided with a second limiting protrusion 370, second limiting slots 313 in communication with the above-mentioned sliding guide slots 311 may be arranged at one or more fixed positions on the limiting frame 310 of the second limiting device 300, and the above-mentioned elastic piece 321, in a second state, may actuate the second limiting protrusion 370 to fit with the second limiting slot 313. For example, when the elastic piece 321 moves to actuate the second limiting protrusion 370 on the elastic piece to one of the fixed positions on the limiting frame 310, the elastic piece 321 may be released to rebound so as to be in the second state, and then the second limiting protrusion may rebound along with the elastic piece and may be located in the second limiting slot 313, so as to stop a further movement of the elastic piece 321.

In the embodiment of the present invention, the second limiting device 300 may be pivotally connected to the bottom plate 100 via the limiting frame 310, for example, the limiting frame 310 can be pivotally connected to the bottom plate 100 by means of a pivot shaft 400, so that the second limiting device 300 can rotate around the pivot shaft 400 relative to the bottom plate 100.

Optionally, in the embodiment of the present invention, a signal interface terminal may be installed on at least one mounting member of the limiting device, and the signal interface terminal is used to connect to the signal interface of the X-ray detector. For example, in FIG. 1, a signal interface terminal 280 is installed at least on the mounting member 220 of the first limiting device 200, and specifically, the signal interface terminal 280 may be installed between the stop blocks 241 and 242. In another embodiment, signal interface terminals may also be arranged on the mounting member 230 of the first limiting device 200, the mounting member 320 or the mounting member 330 of the second limiting device 300.

Optionally, in the embodiment of the present invention, at least one mounting member of the limiting device may form a U-slot together with the stopper on the mounting member. Specifically, in FIG. 1, at least one mounting member of the two mounting members 220, 230 of the first limiting device 200 and the two mounting members 320, 330 of the second limiting device 300 may form a U-slot together with the stopper on the mounting member. For example, the stoppers 340 and 350 of the second limiting device 300 may be configured to be an L-shaped or hook-like stop piece, so that U-slots are respectively formed between the mounting member 320 and the stopper 340 and between the mounting member 330 and the stopper 350, and the X-ray detector can be fixed by the U-slots, so as to prevent the X-ray detector from falling when the support device for an X-ray detector of the embodiment is vertically placed.

Optionally, in the embodiment of the present invention, at least one stopper of the limiting device may be an elastic stopper, and specifically, in FIG. 1, one stopper of the two stoppers 220, 230 of the first limiting device 200 and the two stoppers 320, 330 of the second limiting device 300 may be configured to be an elastic stopper. For example, in this embodiment, at least the stopper 350 is configured to be an elastic stopper, so that the stopper 350 first deforms upwards before the X-ray detector is placed, and the stopper 350 is released and automatically clipped on the side edge of the X-ray detector after the X-ray detector is placed, which facilitates the mounting and dismounting of the X-ray detector.

In another embodiment of the present invention, an X-ray detection device is further provided, comprising an X-ray detector and the support device for an X-ray detector in the above-mentioned embodiment.

In the X-ray detection device and the support device for an X-ray detector of the present invention, the limiting device is pivotally connected to the bottom plate, two mounting members are arranged on the limiting frame of the limiting device, each of the mounting members is provided with a stopper, and since the mounting member can move in a particular direction and be limited at one fixed position on the limiting frame, the corresponding fixed position on the limiting frame can be determined according to the size of the X-ray detector, so that when the two mounting members move to the fixed position, the distance between the two stoppers on the mounting members is identical to the size of one X-ray detector, enabling the X-ray of this size to be fixed between the two stoppers. Moreover, by driving the mounting member from one fixed position to another fixed position and limiting the mounting member at the latter fixed position, the distance between the two stoppers may be changed and adapted to the size of another X-ray detector, facilitating the replacement with X-ray detectors having different sizes.

Some exemplary embodiments have been described above. However, it should be understood that various modifications can be made. For example, if the techniques as described are executed in a different order and/or if the components in the system, architecture, device or circuit as described are combined in different ways and/or are replaced or supplemented with a further component or an equivalent thereof, an appropriate result can be achieved. Accordingly, other embodiments also fall within the scope for protection of the claims.

What is claimed is:

1. A support device for an X-ray detector comprising:
   a bottom plate; and
   a limiting device mounted on the bottom plate, the limiting device comprising:
   a limiting frame;
   two mounting members connected to the limiting frame, at least one of the two mounting members being configured to be able to move in a particular direction and to be limited at one of a plurality of fixed positions on the limiting frame; and
   two stoppers respectively arranged on the two mounting members for limiting the movement of the X-ray detector in the particular direction;
   wherein the limiting device is mounted on a side of the bottom plate that interfaces with the X-ray detector when the X-ray detector is coupled to the support device, and wherein the limiting frame, the two mounting members, and the two stoppers are mounted on a same side of the bottom plate;
   wherein the limiting device includes a first limiting device, and in the first limiting device, the particular direction includes a first direction, and the two mounting members are configured to be able to synchronously move towards each other or away from each other in the first direction; and
   wherein the first limiting device further comprises a gear mounted on the bottom plate, and in the first limiting device, each of the two mounting members is provided with a spur gear, and the spur gears on the two mounting members are parallel to each other and are engaged with the gear.

2. The support device for an X-ray detector according to claim 1, wherein the gear is pivotally connected to the bottom plate.

3. The support device for an X-ray detector according to claim 2, wherein, in the first limiting device, the limiting frame comprises two parallel guide bars arranged in the first direction, each of the mounting members comprises a sliding piece and a mounting piece, the sliding piece and the mounting piece of each of the mounting members are connected to each other to form an L-shaped structure, the sliding pieces of the two mounting members are parallel to each other, and the sliding pieces of the two mounting members are configured to be respectively mounted on the two guide bars and to be able to slide under the guidance by the corresponding guide bars.

4. The support device for an X-ray detector according to claim 1, wherein the first limiting device further comprises a limiting handle which is arranged on at least one of the two mounting members and is provided with a first limiting protrusion, and in the first limiting device, first limiting slots are provided on the plurality of fixed positions of the limiting frame, and the limiting handle is configured to be able to move along with the corresponding mounting member when the limiting handle is at a first position and fit with a first limiting slot when the limiting handle is at a second position.

5. The support device for an X-ray detector according to claim 4, wherein the limiting handle is hinged with the stopper on the corresponding mounting member, and the limiting handle is configured to be able to rotate relative to the corresponding stopper to the first position or the second position.

6. The support device for an X-ray detector according to claim 5, wherein the limiting handle is hinged to the corresponding stopper via a spring hinge.

7. The support device for an X-ray detector according to claim 1, wherein the limiting device includes a second limiting device, and in the second limiting device, the limiting frame is mounted on the bottom plate, at least one of the two mounting members comprises an elastic piece, the particular direction includes a second direction, the limiting frame is provided with a sliding guide slot, and the elastic piece is configured to be able to, in a first state, move in the second direction under the guidance of the sliding guide slot.

8. The support device for an X-ray detector according to claim 7, wherein the limiting frame is pivotally connected to the bottom plate.

9. The support device for an X-ray detector according to claim 7, wherein in the second limiting device, the elastic piece is provided with a second limiting protrusion, second limiting slots are further provided on the plurality of fixed positions of the limiting frame and are in communication with the sliding guide slot, and the elastic piece is configured to be able to, in a second state, actuate the second limiting protrusion to fit with the second limiting slot.

10. The support device for an X-ray detector according to claim 1, wherein a signal interface terminal is installed on at least one of the mounting members of the limiting device, and the signal interface terminal is used to connect to a signal interface of the X-ray detector.

11. The support device for an X-ray detector according to claim 1, wherein at least one of the mounting members of the limiting device forms a U-slot together with the stopper on the mounting member.

12. The support device for an X-ray detector according to claim 1, wherein at least one of the stoppers of the limiting device is an elastic stopper.

13. The support device for an X-ray detector according to claim 1, wherein the support device for an X-ray detector comprises a plurality of the limiting devices stacked in sequence.

14. An X-ray detection device, comprising an X-ray detector and the support device for an X-ray detector according to claim 1.

15. A support device for an X-ray detector comprising:
   a bottom plate; and
   a limiting device mounted on the bottom plate, the limiting device comprising:
   a limiting frame;
   two mounting members connected to the limiting frame, at least one of the two mounting members being configured to be able to move in a particular direction and to be limited at one of a plurality of fixed positions on the limiting frame; and two stoppers respectively arranged on the two mounting members for limiting the movement of the X-ray detector in the particular direction;

wherein the limiting device is mounted on a side of the bottom plate that interfaces with the X-ray detector when the X-ray detector is coupled to the support device, and wherein the limiting frame, the two mounting members, and the two stoppers are mounted on a same side of the bottom plate;

wherein the limiting device includes a first limiting device, and in the first limiting device, the particular direction includes a first direction, and the two mounting members are configured to be able to synchronously move towards each other or away from each other in the first direction; and wherein the first limiting device further comprises a limiting handle which is arranged on at least one of the two mounting members and is provided with a first limiting protrusion, and in the first limiting device, first limiting slots are provided on the plurality of fixed positions of the limiting frame, and the limiting handle is configured to be able to move along with the corresponding mounting member when the limiting handle is at a first position and fit with a first limiting slot when the limiting handle is at a second position.

16. A support device for an X-ray detector comprising:
a bottom plate; and
a limiting device mounted on the bottom plate, the limiting device comprising:
   a limiting frame;
   two mounting members connected to the limiting frame, at least one of the two mounting members being configured to be able to move in a particular direction and to be limited at one of a plurality of fixed positions on the limiting frame; and
   two stoppers respectively arranged on the two mounting members for limiting the movement of the X-ray detector in the particular direction;
wherein the limiting device is mounted on a side of the bottom plate that interfaces with the X-ray detector when the X-ray detector is coupled to the support device, and wherein the limiting frame, the two mounting members, and the two stoppers are mounted on a same side of the bottom plate;
wherein the limiting device includes a second limiting device, and in the second limiting device, the limiting frame is mounted on the bottom plate, at least one of the two mounting members comprises an elastic piece, the particular direction includes a second direction, the limiting frame is provided with a sliding guide slot, and the elastic piece is configured to be able to, in a first state, move in the second direction under the guidance of the sliding guide slot.

* * * * *